United States Patent [19]

Mestrallet et al.

[11] 4,368,061

[45] Jan. 11, 1983

[54] METHOD OF AND APPARATUS FOR MANUFACTURING ETHYLENE

[75] Inventors: Joëlle Mestrallet, Asnieres; Gérard Heck, Louveciennes; Victor Kaiser, Maisons Laffitte, all of France

[73] Assignee: Compagnie Francaise d'Etudes et de Construction "Technip", Paris, France

[21] Appl. No.: 156,382

[22] Filed: Jun. 4, 1980

[30] Foreign Application Priority Data

Jun. 6, 1979 [FR] France .................... 79 14449

[51] Int. Cl.³ .............................................. F25J 3/02
[52] U.S. Cl. .................................... 62/28; 62/24; 208/351
[58] Field of Search ..................... 62/24-28; 208/351

[56] References Cited

U.S. PATENT DOCUMENTS 2,938,934  5/1960  Williams ................. 62/28
3,073,129  1/1963  Grenier .................. 62/28
3,595,782  7/1971  Bucklin et al. ........... 62/27

Primary Examiner—Norman Yudkoff
Attorney, Agent, or Firm—Kenyon & Kenyon

[57] ABSTRACT

A method of making ethylene consisting in processing an ethylene gas condensate which is passed through a de-ethanizer to separate as gases the $C_2$-hydrocarbons with two carbon atoms, cooling said hydrocarbons to condensate a part thereof, feeding said hydrocarbons into a separator where the condensed phase is separated and recycled to the de-ethanizer, and feeding the non-condensed fraction of said hydrocarbons into an ethylene-recovering unit with which is associated a reboiling system for heating the fluid taken from said unit prior to recycling it to the latter, and further comprising the step of exchanging heat between the hydrocarbons from the de-ethanizer and the reflux fluid from said reboiling system so as to at least partially condensate the hydrocarbons fed to said separator.

7 Claims, 1 Drawing Figure

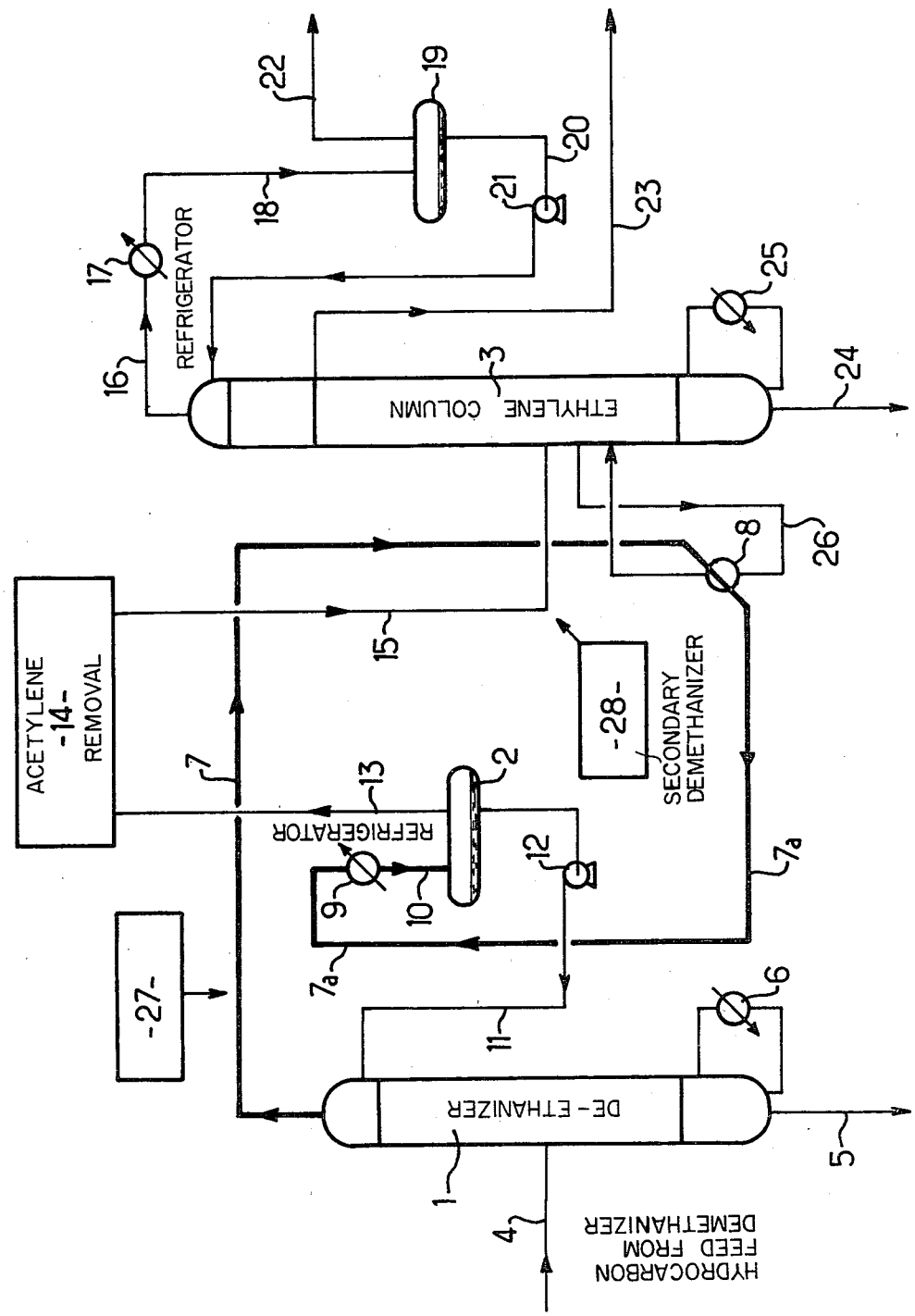

METHOD OF AND APPARATUS FOR MANUFACTURING ETHYLENE

The present invention relates essentially to an improved method of making ethylene.

It is also directed to an apparatus or plant for producing ethylene to carry out said method.

There are already known ethylene manufacturing units which make essentially use of a de-ethanization column as well as an ethylene superfractionating section. Such units of course include a number of machines such as for instance various compressors which require a substantial power supply for operating same.

The energy consumption of these various machines obviously depends on many factors such as the capacity of the production unit, the method adopted, the climatic conditions and so on but in spite of this the present ethylene production units are still consuming high amounts of power.

Therefore a main object of the present invention is in particular to remove such an inconvenience by providing an improved method of and apparatus or plant for producing ethylene with which a substantial decrease in the power consumption may be achieved by providing a particular mode of condensing the gaseous hydrocarbons issuing from the de-ethanizer column.

For this purpose the invention provides an improved method of making ethylene, of the type consisting in treating a condensate of ethylene gas which is passed into a de-ethanizer to separate in a gaseous condition the $C_2$-hydrocarbons with two carbon atoms, cooling these hydrocarbons to condensate a part thereof, feeding these hydrocarbons into a separator where the condensed phase is separated and recycled to the de-ethanizer, and feeding the non-condensed fraction of these hydrocarbons to an ethylene recovering unit with which is associated a reboiling system to heat the fluid withdrawn from said unit before recycling it into the latter, the method being essentially characterized in that with a view to substantially reducing the power consumption, a heat exchange is effected between the hydrocarbons issuing from the de-ethanizer and the reflux fluid from the reboiling system associated with the ethylene recovering unit in order to obtain the at least partial condensation of the hydrocarbons fed to the separator.

According to another characterizing feature of the method of the invention, after said heat exchange, the cooled hydrocarbons are subjected to an additional refrigerating step.

It should be added that said heat exchange is carried out according to the invention at an additional reboiler associated with an ethylene superfractionating section.

The invention also relates to an ethylene production plant or apparatus for carrying out said method and of the kind comprising at least one de-ethanizer connected through the agency of a separator drum to an ethylene superfractionating section comprising at least one reboiler acting as a heat exchanger which comprises a heating fluid circuit and a cooling fluid circuit consisting of a circuit of reflux into said superfractionating section, this apparatus being characterized in that the head of the de-ethanizer is connected to the separator drum through a pipe-line which extends through said reboiler to form said heating fluid circuit thereof which heating fluid is itself cooled down before being conveyed to the separator drum.

This reboiler consists of an additional reboiler associated with an ethylene superfractionating tower.

In other words owing to a proper selection of the operating pressures of the de-ethanizer and superfractionating columns, it is possible to obtain temperatures such as to recover at the additional reboiler the cold available in the superfractionating column so as to transfer said cold to the de-ethanizer via the separator.

According to a further characterizing feature of the invention, said pipe-line extends advantageously through an additional heat exchanger provided between the additional reboiler and said separator drum.

It should moreover be pointed out that in an apparatus according to the invention the operating pressure and temperature at the head of the de-ethanizer are respectively lying between about 18 bars and 33 bars and between about $-5°$ C. and $-25°$ C., whereas the operating pressure and temperature of the separator drum are respectively lying between the same values upon neglecting the head losses and the operating pressure at the head of the superfractionating column is lying between about 15 bars and 25 bars and the operating temperature of the additional reboiler is lying between about $-10°$ C. and $-30°$ C.

Preferred pressure and temperature values are given in the following detailed description in which other characterizing features and advantages of the invention will be described with reference to the accompanying diagrammatic drawing given by way of non-limiting example only wherein the single FIGURE shows an ethylene production unit embodying the improvements according to the invention.

According to an examplary embodiment and with reference to said FIGURE, an ethylene production apparatus of the kind involved by the invention essentially comprises a de-ethanizer column 1 hereinafter referred to as de-ethanizer and connected through the agency of a separator drum 2 to an ethylene superfractionating tower 3.

The other parts or elements of the apparatus will be described in detail hereinafter together with its operation.

At first an ethylene-rich gas is compressed and then cooled down and condensed so as to be fractionated through distillation. A first fractionating column (not shown) would separate the methane. It is the tower bottoms or still residue of such a distillation which are fed into the de-ethanizer 1 through the duct 4 shown on the drawing. This de-ethanizer provides at a top portion thereof for the separation in the gaseous condition of $C_2$-hydrocarbons having two carbon atoms whereas the $C_3$-, $C_4$-, etc. hydrocarbons obtained at the bottom of the de-ethanizer are conveyed through a duct 5 into another section (not shown) of the unit. At 6 is shown a reboiler associated with the lower portion of the de-ethanizer 1. As well known in the art the heat supply required for the reboiling of the de-ethanizer 1 is provided through heat exchange with a heating fluid or through recovering of steam condensation heat.

The gaseous products from the head of column 1 where the temperature is for instance of $-12°$ C. are fed into a duct 7 which according to the invention extends through an additional or intermediate reboiler 8 associated with the superfractionating tower 3. Thus as explained in detail hereinafter the hydrocarbons from the head of column 1 will give up heat while being cooled down to a temperature for instance of about $-13.5°$ C. so as to already condense at least partially and be conveyed through the portion 7a of the duct 7 into a heat exchanger 9 where they will receive cold from a refrigerating fluid which is vaporizing and which consists for instance of propane or propylene. The hydrocarbons thus condensed in part will flow through the duct 10 into the separator drum where the temperature is of −14° C. for instance.

The liquid hydrocarbons are recycled to the head of the de-ethanizer 1 by passing into a duct 11 provided with a pump 12 whereas the hydrocarbons vapors are fed through the duct 13 into a section 14 where acetylene is removed through hydrogenation or any other process.

It should be noted that the heat exchanger 9, arranged between the reboiler 8 and the separator 2, is not at all compulsory for the operation of the unit according to the invention. It is used somewhat as a cold-make-up heat exchanger since if need be it supplies additional cold for the condensation of the hydrocarbons issuing from the duct portion 7a. This make-up or additional supply of cold for instance by means of a heat exchanger 9 may be carried out automatically in accordance with the needs. Such a heat exchanger may however be useful for adjusting the pressure in the de-ethanizer 1 and also for providing a good start-up of the unit.

Reverting to the section 14 which provides for the removal of acetylene through hydrogenation or any other suitable process the gaseous hydrocarbons will issue from said section through a duct 15 to feed the superfractionating tower 3.

The hydrocarbon gases at the head of this tower 3 are passed through a duct 16 into a heat exchanger 17 where they receive cold from a refrigerating fluid which is vaporizing, such as for instance propylene or propane. Then the hydrocarbons enter a separator 19 through a duct 18, the liquid phase being returned as a reflux to the head of the tower 3 through a duct 20 fitted with a pump 21 and the gaseous phases consisting of the hydrocarbon vapors and containing light impurities is recycled through a duct 22 to a compressor section (not shown). At 23 is shown a pipe-line through which the ethylene produced is taken or withdrawn sidewise from the column 3. At 24 is shown a pipe-line for recovering the bottoms from the superfractionating tower 3 and in particular ethane which would result partially from the hydrogenation of acetylene at 14 and which is recycled as a partial load of the ethylene production unit.

All the arrangements set forth in the foregoing paragraph are known per se as well as the reboiling system of the tower 3 which according to the examplary embodiment shown consists of a reboiler 25 at the bottom of the tower 3 which recovers the heat of a fluid used as a heating fluid, such as the condensation heat of a certain amount of refrigerating fluid and through the intermediate and additional reboiler 8 which has been mentioned hereinabove.

A particular attention should be paid to this intermediate reboiler 8 which plays a particular role according to the invention. This reboiler indeed works as a heat exchanger which comprises a refrigerating fluid circuit consisting of a circuit 26 of reflux into the superfractionating tower 3 and of a heating fluid circuit which is nothing else than the duct 7 carrying the hydrocarbon gases issuing from the head of the de-ethanizer 1. In other words these hydrocarbon gases which are reaching the intermediate reboiler at a temperature of about −12° C. will give up heat to the reflux circuit 26 which is at a temperature of about −19° C. and are accordingly cooled down to a temperature of about −13.5° C. at the outlet of the reboiler 8 before feeding the heat exchanger 9 and then the separator drum 2.

The pressure and temperature values given hereinafter for the de-ethanizer 1 and separator 2 as well as for the superfractionating tower 3 are illustrative of the operating conditions of a production unit according to the invention.

The operating pressure at the head of the de-ethanizer 1 is comprised between about 18 bars and 33 bars and is preferably equal to 26.5 bars. The temperature at the head of the de-ethanizer is comprised between about −5° C. and −25° C. and is preferably equal to −12° C. as previously mentioned.

The operating pressure of the separator is comprised between about 17 bars and 32 bars and is preferably equal to 26 bars. The temperature of the separator is comprised between about −7° C. and −23° C. and is preferably equal to −14° C.

At last the operating pressure at the head of the superfractionating tower 3 is comprised between about 15 bars and 25 bars and is preferably equal to 18 bars whereas the intermediate reboiling temperature is comprised between about −10° C. and −30° C. and is preferably equal to −19° C. as stated previously.

Thus have been provided according to the invention a method and an apparatus for manufacturing ethylene through which it is possible to recover the cold available in a superfractionating tower in order to transfer it through reflux into a de-ethanizer and this owing to a proper selection of the operating pressures. Owing to the invention the power consumed by the main refrigeration plant or device is advantageously decreased by at least 10%.

It should be understood that the invention is not at all limited to the embodiment described and shown which has been given by way of illustrative example only.

If for instance the acetylene content is high it is well possible within the scope of the invention to hydrogenate the acetylene no longer with the hydrocarbon vapors collected at 14 but directly with the whole of the product issuing from the head of the de-ethanizer 1 as diagrammatically shown at 27. Likewise if the methane content is substantial a secondary de-methanizer 28 may be provided upstream of the ethylene purification tower 3.

The invention therefore comprises all the technical equivalents of the means described as well as their combinations if same are carried out according to its gist and used within the scope of the appended claims.

What is claimed is:

1. In a method for recovering ethylene from a condensate of ethylene gas comprising the steps of passing said condensate to a de-ethanizer and recovering therefrom in a gaseous condition hydrocarbons containing two carbon atoms, cooling said hydrocarbons to at least partially condense said hydrocarbons, separating the condensed and non-condensed phases, recycling said condensed phase to said de-ethanizer and feeding said non-condensed phase to an ethylene recovery unit having associated therewith a reboiling system for heating fluid taken from said unit prior to recycle of said fluid to said unit, the improvement comprising effecting an additional heat exchange in an additional and intermediate reboiler system associated with said unit, said additional heat exchange being effected between said gaseous hydrocarbons containing two carbons recovered from said de-ethanizer and the recycling liquid from said ethylene recovery unit in said additional and intermediate reboiler system, and wherein the head of the de-ethanizer is operating at a pressure of between about 18 and 33 bars and a temperature between about $-5°$ C. and $-25°$ C., and the head of the ethylene recovery unit is operating at a pressure of between about 15 and 25 bars.

2. A method according to claim 1, wherein the separator is at an operating pressure of between about 17 to 32 bars and an operating temperature of between about $-7°$ C. and $-23°$ C., and said additional and intermediate reboiler is at an operating temperature of between about $-10°$ C. and $-30°$ C.

3. A method according to claim 2 wherein, after said hydrocarbons are cooled by heat exchange carried out at said intermediate reboiler, the cooled hydrocarbons are subjected to an additional refrigeration step.

4. In an ethylene recovery apparatus comprising at least one de-ethanizer connected through a vapor/liquid separator to an ethylene recovery unit having associated therewith a reboiler system comprising a first reboiler located at the bottom of said ethylene recovery unit, the improvement wherein said reboiler system includes an additional reboiler located at an intermediate position on the ethylene recovery unit, each of said reboilers having a heating fluid circuit and a refrigerating circuit, the heating fluid circuit of said first reboiler being an external heating fluid circuit, and the refrigerating fluid circuit of said first reboiler being a circuit of fluid which is taken from said ethylene recovery unit and recycled to the bottom of said unit, the refrigerating fluid circuit of said additional reboiler comprises a circuit of recycling fluid into said superfractionating section, and the heating fluid circuit of said additional reboiler comprises a duct connecting the heat of said de-ethanizer to said separator, and wherein said apparatus is adapted to operate such that the head of said de-ethanizer is at an operating pressure of between about 18 and 33 bars and an operating temperature of between about $-5°$ C. and $-25°$ C. and the head of said ethylene recovery unit is at an operating pressure of between about 15 and 25 bars.

5. An apparatus according to claim 4, wherein said separator is adapted to operate at an operating pressure between about 17 to 32 bars and an operating temperature between about $-7°$ C. and $-23°$ C. respectively, and second reboiler is adapted to operate at an operating temperature between about $-10°$ C. and $-30°$ C.

6. An apparatus according to claim 4, wherein said duct extends through an additional heat exchanger provided between said additional reboiler and said separator.

7. An apparatus according to claim 6, wherein said de-ethanizer is adapted to operate at a head pressure of 26.5 bars, said ethylene recovery unit is adapted to operate at a head pressure of 18 bars, said separator is adapted to operate at a temperature of $-14°$ C. and said additional reboiler is adapted to operate at a temperature of $-19°$ C.

* * * * *